United States Patent
Bzdusek et al.

(10) Patent No.: US 11,020,614 B2
(45) Date of Patent: Jun. 1, 2021

(54) RADIATION THERAPY OPTIMIZATION UNIT WITH GLOBAL CONSIDERATIONS

(71) Applicant: KONINKLIJKE PHILIPS N.V., Eindhoven (NL)

(72) Inventors: Karl Antonin Bzdusek, Madison, WI (US); Prashant Kumar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 335 days.

(21) Appl. No.: 15/572,628

(22) PCT Filed: May 23, 2016

(86) PCT No.: PCT/IB2016/053000
§ 371 (c)(1),
(2) Date: Nov. 8, 2017

(87) PCT Pub. No.: WO2016/198979
PCT Pub. Date: Dec. 15, 2016

(65) Prior Publication Data
US 2018/0154177 A1    Jun. 7, 2018

Related U.S. Application Data

(60) Provisional application No. 62/172,267, filed on Jun. 8, 2015.

(51) Int. Cl.
*A61N 5/10* (2006.01)

(52) U.S. Cl.
CPC ......... *A61N 5/1031* (2013.01); *A61N 5/1039* (2013.01); *A61N 5/1047* (2013.01); *A61N 5/1077* (2013.01)

(58) Field of Classification Search
CPC .... A61N 5/103–1039; A61N 2005/1032–1041
See application file for complete search history.

(56) References Cited

U.S. PATENT DOCUMENTS

| | | |
|---|---|---|
| 2004/0001569 A1 | 1/2004 | Luo |
| 2005/0207531 A1 | 9/2005 | Dempsey et al. |
| 2007/0201614 A1 | 8/2007 | Goldman et al. |
| 2008/0008291 A1 | 1/2008 | Alakuijala et al. |
| 2010/0232572 A1 | 9/2010 | Nord et al. |
| 2012/0136194 A1* | 5/2012 | Zhang .................. A61N 5/103 600/1 |
| 2014/0073831 A1 | 3/2014 | Hirayama et al. |
| 2015/0141733 A1 | 5/2015 | Kumar et al. |

(Continued)

OTHER PUBLICATIONS

Rosen, I. et al. "Interactively exploring optimized treatment plans." Inc. J. Radiat Oncol Biol Phys. vol. 61, Issue 1, (2005), pp. 570-582.

(Continued)

*Primary Examiner* — Catherine B Kuhlman (57) ABSTRACT

A radiation therapy planning system (100) includes a radiation therapy optimization unit (124), which receives at least one target structure and at least one organ-at-risk (OAR) structure segmented from a volumetric image, and generates an optimized plan (126) based on at least one modified objective function. The optimized plan (126) includes a planned radiation dose for each voxel.

19 Claims, 3 Drawing Sheets

(56) References Cited

U.S. PATENT DOCUMENTS

2017/0173365 A1    6/2017  Bzdusek et al.

OTHER PUBLICATIONS

Gopal, R. et al., "Plan space: Representation of treatment plans in multidimensional space," Int J Radiat Oncol Biol Phys 2002; 53: 1328-36.

Zhang, X. et al., "A sensitivity-guided algorithm for automated determination of IMRT objective function parameters," Med Phy 2006; Abstract.

Zhang, H.H. et al. "Modeling plan-related clinical complications using machine learning tools in a multiplan IMR framework." Int J Radiat Oncol Biol Phys 2009; 74: 1617-26.

Binbin, W. et al., "Data driven approach to generating achievable dose volume histogram objectives in intensity modulated radiation therapy treatment planning." Int J Radiat Oncol Biol Phys 2011; 79:1241-7.

Craft, D.L. et al., "Improved planning time and plan quality through multicriteria optimization for intensity modulated radiotherapy." Int J Radiat Oncol Biol Phys, vol. 82, No. 1, pp. e83-390, 2012.

Wu, B. et al., "Patient geometry-driven information retrieval for IMRT treatment plan quality control." Med Phys 2009; 36: 5497-505.

Petit, S.R. et al., "Increased organ sparing using shape-based treatment plan optimization for intensity modulated radiation therapy of pancreatic adenocarcinoma." Radiotherapy and Oncology 102 (2012) 38-44.

Wu, B. et al. "Using overlap volume histogram and intensity modulated radiation therapy plan data to guide automate volumetric modulated arc therapy treatment planning: a head and neck case study", Int J Radiat Oncol Biol Phys 2012; Abstract.

Wu, B. et al., "A knowledge based and patient geometry specific automated IMRT treatment planning system." Medical Physics 37(6):338—Jun. 2010, Abstract.

Moore, K.L. et al., "Low Quantitative Metrics for Assessing Plan Quality." Semin Radiat Oncol 2012 22:62-69.

* cited by examiner

RADIATION THERAPY OPTIMIZATION UNIT WITH GLOBAL CONSIDERATIONS

CROSS-REFERENCE TO PRIOR APPLICATIONS

This application is the U.S. National Phase application under 35 U.S.C. § 371 of International Application Serial No. PCT/IB2016/053000, filed on May 23, 2016, which claims the benefit of U.S. Application Ser. No. 62/172,267, filed on Jun. 8, 2015. This application is hereby incorporated by reference herein.

FIELD OF THE INVENTION

The following generally relates to external beam radiation therapy, and is described with particular application to inverse planning optimization techniques, which include Intensity Modulate Radiation Therapy (IMRT) and/or Volumetric Modulated Arc Therapy (VMAT) radiation therapy planning.

BACKGROUND OF THE INVENTION

VMAT and/or IMRT radiation therapy techniques deliver high doses to target areas, such as cancerous growth, to destroy or control diseased tissues in the target area. Dose goals are identified by a healthcare practitioner based on one or more volumetric planning images, e.g. an X-ray Computed Tomography (CT) image. Based on the dose goals an optimizer is used to plan the orientation, duration, shape and intensity of beams of external radiation to the target areas. Targets areas and nearby organs or organs-at-risk (OARs) are identified in the planning images and are typically segmented as structures.

In delivering the beams of external radiation, which pass through the body from a radiation source, organs in the path of the radiation beams are also subject to the delivered radiation. Organs can be classified as serial organs or parallel organs. Serial organs, such as a brain stem, spinal cord, etc., which receive lethal doses of radiation to any one part of the serial organ causes the entire organ to fail. Parallel organs, such as a parotid gland, larynx, lips, etc. can receive lethal doses to a portion of the parallel organ and still maintain at least some function from the remaining portions.

Planning methods for the beams of external radiation typically include competing objectives. Some objectives call for delivering radiation to target areas. Other objectives call for not delivering radiation or only permitting delivery of a certain amount to OARs. OAR objectives typically include a maximum dose goal or maximum dose volume histogram (DVH), and a weight or priority of the objective relative to other OAR objectives. Target objectives include a minimum radiation dose goal or uniform dose goal. An optimizer program inputs the target and OAR objectives with the dose goals and identifies a set of beams, each of an intensity, duration, shape, and orientation, which optimally meet the competing objectives to form a plan. The weights correspond to segmented volumes, such as the OARs and target areas, for which a planned dose is computed using weight applied to the entire segmented volume based on the weighted objective.

A healthcare practitioner reviews the output from the optimizer typically viewed as planned or expected doses expressed volumetrically, such as iso-contours imposed on the planning image, dose volume histograms, and the like. In a tuning process, objectives can be changed, e.g. change a weight or a dose goal, or objectives can be added. The added objectives can direct the dose, such as more to certain targets areas or less to certain OARs. The added objectives can include subsets of the segmented structures or additional structures with corresponding dose goals to alter or shift planned doses. The optimizer program is re-run with the changed/additional objectives, and the process repeated until an acceptable optimized plan is reached. However, adding more structures and objectives imposes greater complexity, more time by the practitioner, and greater computing requirements, e.g. slower and/or longer response times, more computer hardware, etc.

Manual review and directing the optimizer increases time by valuable clinical staff, decreasing throughput and increasing cost. Manual review can also be inconsistent. Automating the planning process can reduce the number of interactions for review, analysis and changes by the healthcare practitioner.

SUMMARY OF THE INVENTION

Aspects described herein address the above-referenced problems and others.

The following describes a radiation therapy (RT) optimization unit with global considerations of a radiation therapy planning system and method. The RT optimization unit determines planned radiation doses for target structures and OAR structures using a new class of objective functions which are based on standard dose objective functions modified to drive harder to meet the input goal and continue to drive beyond the goal but at a reduced level. The global considerations include an overlap and/or a distance between target structures and OAR structures, dose fall off regions from the target structures, a body or integral dose minimization, reducing doses to OAR structures beyond dose goals where possible, and increasing dose uniformity and conformity to target structures when desired. In some embodiments, optimization parameter tuning is incorporated directly into the optimization.

In one aspect, A radiation therapy planning system includes a RT optimization unit, which receives at least one target structure and at least one organ-at-risk radiation (OAR) structure segmented from a volumetric image, and generates an optimized plan based on at least one modified objective function. The optimized plan includes a planned radiation dose for each voxel.

In another aspect, a method of radiation therapy planning includes segmenting at least one target structure and organ-at-risk (OAR) structures from a volumetric image. An optimized plan is generated based on at least one modified objective function, and the optimized plan includes a planned radiation dose for each voxel inside the user specified dose grid.

In another aspect, a method of radiation therapy planning includes segmenting at least one target structure and organ-at-risk (OAR) structures from a volumetric image. An optimized plan is generated based on at least one modified objective function, and the optimized plan includes a planned radiation dose for each voxel inside the user specified dose grid. The optimized plan is iteratively adjusted and at least one of a dose goal and/or a weight for at least one voxel is adjusted between at least one iteration.

In another aspect, a computing system includes a processor configured to receive dose goals and weights for at least one target structure and organ-at-risk (OAR) structures segmented from a volume according to a volumetric image. The processor is further configured to weight voxels in a volume of the volumetric image according to a distance from a nearest one of the at least one target structure, and generate an optimized plan based on at least one objective function. The optimized plan includes a planned radiation dose for each voxel in the volume. The optimized plan is iteratively adjusted and at least one of a dose goal and a weight for at least one voxel is adjusted between at least one iteration.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF EMBODIMENTS

Figure 1:
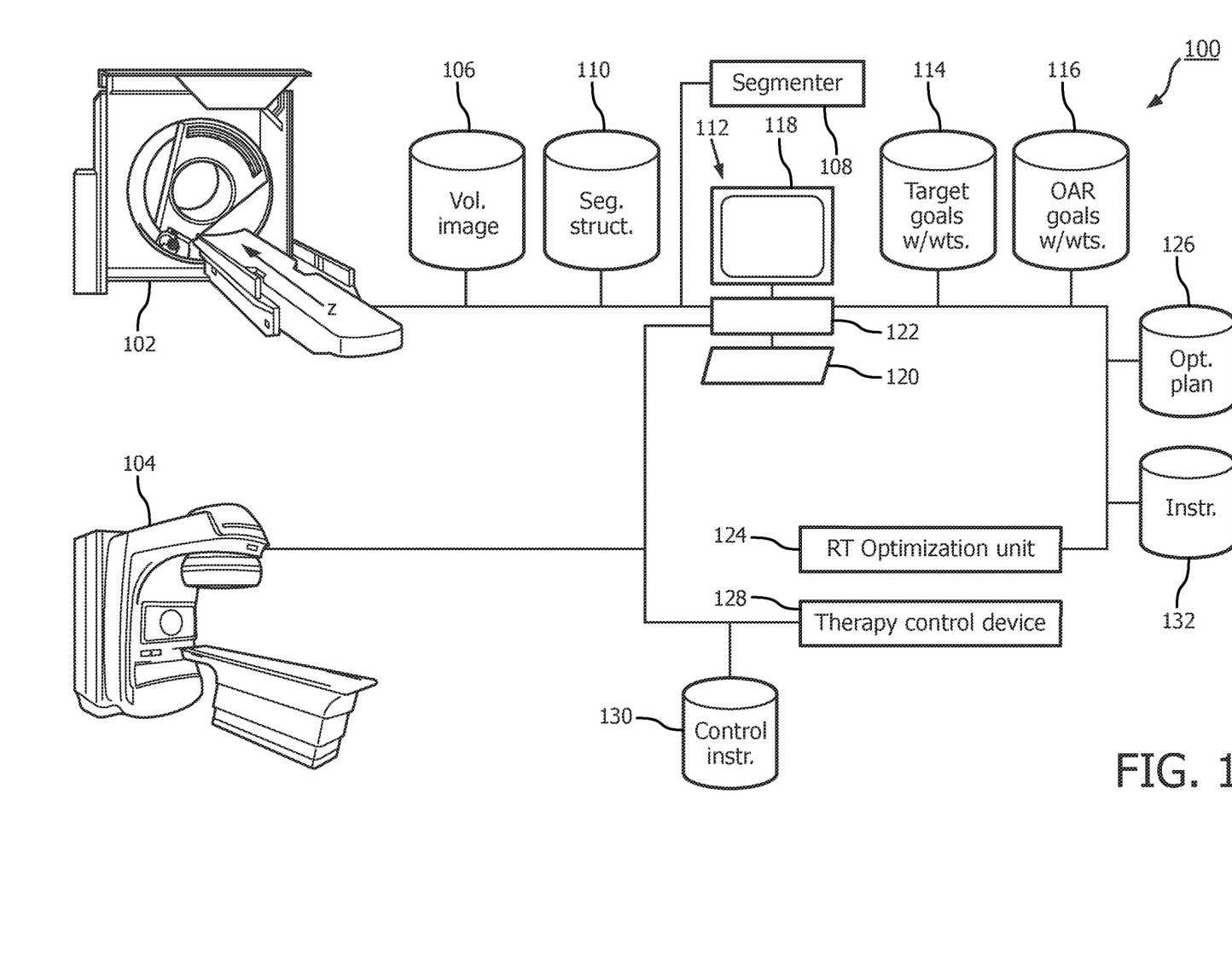
FIG. 1 schematically illustrates an example system including a RT optimization unit with global considerations, in connection with an imaging and a radiation delivery system.

Initially referring to FIG. 1, an example system 100 in connection with an imaging device 102 and a radiation delivery device 104 is schematically illustrated. The imaging device 102 includes a scanner of one or more modalities such as an X-ray Computed Tomography (CT) scanner, Magnetic Resonance Imaging (MRI) scanner, a Positron Emission Tomography (PET) scanner, a Single Proton Emission Computed Tomography (SPECT) scanner, combinations, hybrids and the like, which generates a volumetric image 106 of a region of interest (ROI) of a subject used to plan the radiation therapy. The volumetric planning image 106 includes at least a three-dimensional (3D) image, e.g. volume image constructed from 2D slices, 3D image, 4D image, etc. The volumetric planning image 106 can be received directly from the imaging device 102 or stored in an electronic memory, such a Picture Archiving and Communication System (PACS), a Radiology Information System (RIS), an Electronic Medical Record (EMR), cloud storage, server storage, local storage, and the like.

A segmenter 108 identifies and segments structures 110 from the volumetric planning image 106. The segmenter 108 identifies and segments structures 110 automatically or manually using known or other segmentation techniques. The segmented structures 110 include one or more target structures, such as tumors, diseased tissue, and the like. The segmented structures 110 include one or more OAR structures. The OAR structures include serial and/or parallel organs. Each segmented structure 110 is a volumetric structure and can be defined spatially by a subset of voxels in the volumetric planning image 106. A voxel can be included in more than one segmented structure. For example a target structure can overlap with an OAR structure, such as a portion of the OAR including diseased tissue.

A computing device 112, such as a workstation, laptop, tablet, smart phone, body worn computing device, server, and the like, receives input indicative of target goals 114 and OAR goals 116. The computing device 112 includes a display device 118, one or more input devices 120, and a data processor 122, such as a digital processor, microprocessor, electronic processor, optical processor, multi-processor, and the like. The target goals 114 and OAR goals 116 include radiation dose or biological goals for the segmented structures 110.

A radiation therapy (RT) optimization unit 124 receives the segmented structures 110, target goals 114 and OAR goals 116, and fits a dose grid to a volume or a portion of the volume of the planning image 106. Each dose grid voxel can be represented by at least one goal. In some instances this representation globally reduces or eliminates hot doses outside a target structure. Voxels in the dose grid, which are not included in the OAR structures and/or target structures are included in a dose fall off region, a general body region or some other dose control structure. Each of the dose fall off region and the general body region comprise a volume defined by structure with a dose goal. In one embodiment, a coarse dose grid is initialized, which includes combined voxels, and the coarse dose grid is then refined to a voxel level during optimization based on convergence of an optimization solution. In some instances, this improves the performance of the computing device 112 comprising the RT optimization unit 124.

The RT optimization unit 124 weights voxels based on a distance from a target structure and generates an optimized plan 126 by iteratively computing planned doses using modified objective functions. In one embodiment, the RT optimization unit 124 weights voxels based on a distance from a target structure and generates the optimized plan 126 by iteratively computing planned doses using standard objective functions. The RT optimization unit 124 can adjust weights and/or dose goals during the optimization. In some instances, the RT optimization unit 124 inherently resolves conflicts of overlapping structures using the distance transformed based voxel weighting scheme, which eliminates the overhead of generating additional structures and/or additional goals for overlapping target and OAR structures, thereby improving the performance of the computing device 112. In some instances, the modified objective functions push the computed planned dose beyond the dose goal, and globally considers lower doses to OAR structures and uniform doses to target structures. In some instances, the adjusting of weights and/or dose goals, e.g. self-tuning, reduces demands on the healthcare practitioner and increases planning throughput. In one embodiment, the RT optimization unit generates the optmized plan 126 by iteratively computing planned doses using modified objective functions and the segmented structures 110.

In one embodiment, each modified objective function is processed individually. In another embodiment each dose grid voxel is processed with the corresponding modified objective function(s) for that voxel, which in some instances improves performance for the computing device 112 that comprises multi-thread the voxel-wise processing using multiple processor cores or graphic processing unit (GPU) cores. For example, with processing voxel-wise and a four core processor, each core can be assigned and process the modified objective functions for approximately one quarter of the voxels operating in parallel.

The modified objective functions include a maximum dose OAR modified objective function, a maximum equivalent uniform dose (EUD) OAR modified objective function, and/or a target modified objective function. In one embodiment, the modified objective functions can include standard target objective functions. In one embodiment a maximum dose OAR modified objective function includes a maximum DVH OAR modified objective function, which considers portions of the segmented structure.

The maximum dose OAR modified objective function decreases the planned dose for a voxel $d_i$ lower than the dose goal $d_g$ where the goal has been met. For example, where $d_i - d_g > 0$, the maximum dose OAR modified objective function is defined by:

$$F^k = w^k \sum_{i \in V} w_i \left( \frac{d_i - d_{go}}{d_{go}} \right)^2 \Delta v_i, \qquad \text{EQUATION 1}$$

else the modify maximum dose OAR modified objective function is defined by:

$$F^k = w^k \sum_{i \in V} w_i \left( \frac{f(OFValue_{targets}, c)}{d_{go}} \right)^2 \Delta v_i, \qquad \text{EQUATION 2}$$

where $d_{go} = d_g - d_o$, $d_o$ is a dose offset from goal, $w^k$ is the weight or priority of the $k^{th}$ OAR structure and dose goal, $w_i$ is the weight of voxel i, $f(OFValue_{targets}, c)$ is a residual driver, OFValue is the value(s) of the modified objective function, c is a constant, $v_i$ is the volume of voxel i, and $\Delta v_i$ is the voxel volume relative to the volume V of the $k^{th}$ OAR structure. The residual driver is a constant or function based on target objective function value(s). The OAR goal 116 received or input includes the goal dose ($d_g$), the priority/weight ($w^k$), and the level of sparing (c). In one embodiment, the level of sparing is a constant or function of the goal dose. The level of sparing can be a value of a dose goal where $c < d_g$ or expressed as a function of the goal dose, such as a percentage.

Once the dose goal is met, e.g. $d_i \leq d_g$, the residual driver decreases the planned dose below the goal. A gradient function, which is the derivative of the objective function with an offset to the dose goal ($d_o$), has the effect of increasing the push or decreasing the planned dose to reach the level of dose sparing. In another embodiment, a small offset value is used for EQUATION 2, e.g, $F^k = d_i - x$, where x is a small offset. In one embodiment, the RT optimization unit 124 uses the objective function defined by EQUATION 1 for all values, e.g. a standardized objective function. In some instances this means the objective function operates to just meet the goal. The gradient function for EQUATION 1 where $d_i - d_g > 0$ is defined by:

$$\frac{dF^k}{dd} = \frac{dF^k}{dd} w^k \sum_{i \in V} w_i \left( \frac{d_i^2 - 2 d_{go} d_i + d_{go}^2}{d_{go}^2} \right)^2 \Delta v_i = \qquad \text{EQUATION 3}$$
$$2w^k \sum_i w_i \left( \frac{d_i - d_{go}}{d_{go}^2} \right) \Delta v_i,$$

else the gradient function according to EQUATION 2 is defined by:

$$\frac{dF^k}{dd} = \frac{dF^k}{dd} w^k \sum_{i \in V} w_i \left( \frac{f(OFvalue_{targets}, c)}{d_{go}^2} \right)^2 \Delta v_i = \qquad \text{EQUATION 4}$$
$$2w^k \sum_i w_i \left( \frac{f(OFValue_{targets}, c)}{d_{go}^2} \right) \Delta v_i.$$

For example, in a case of a serial OAR of the spinal cord, a typical maximum dose is 45 Gray(Gy), e.g. maximum OAR dose goal. With a voxel dose value of 50 Gy, a OAR structure weight of 2, a voxel weight of 1, a relative voxel volume of 1, and a dose offset from goal of 2 Gy, the modified objective function value for the voxel is $2*((50-45-2)/(45-2))^2*1 = 0.053$ and the gradient value is $2*2*(50-45-2)/(45-2)^2*1 = 0.015$. With a dose value of 46 Gy, the modified objective function value decreases to $2*((46-45-2)/(45-2)^2*1 = 0.010$ and the gradient is reduced to $2*2*(46-45-2)/(45-2)^2*1 = 0.006$. With a dose value of 44 Gy, then the goal is met for the voxel, e.g. 44 Gy<45 Gy. Using a residual driver value of 1 Gy then the modified objective function value is $2*(1/(45-2))^2*1 = 0.001$ and the gradient is $2*2*1/(45-2)^2*1 = 0.002$. Values of objective functions indicate the success in meeting the objective. Larger values indicate greater distance from the objective of meeting the dose objective for the structure. Gradient functions are used to drive the RT optimization unit to make changes in the planned dose based on changes to the duration, direction, orientation, shape, etc. of the external beams of radiation.

The maximum EUD OAR modified objective function similarly decreases the planned dose for a OAR structure $EUD^k$ lower than the EUD goal $EUD_g$ where the goal has been met. For example, where $EUD^k - EUD_g > 0$ the maximum EUD OAR modified objective function is defined by:

$$F(EUD^k, EUD_{go}) = w^k \left( \frac{EUD^k - EUD_{go}}{EUD_{go}} \right)^2, \qquad \text{EQUATION 5}$$

else the maximum EUD OAR modified objective function is defined by:

$$F(EUD^k, EUD_{go}) = f(OFValue_{targets}, c) \qquad \text{EQUATION 6}$$

where k is the OAR structure being evaluated, $EUD_o$ is an offset from goal, $EUD_{go} = EUD_g - EUD_o$, $w^k$ is a weight or priority of the OAR structure, $w_i$ is a weight of voxel i, $f(OFValue_{targets}, c)$ is the residual driver, $d_i$ is a dose in voxel i, $v_i$ is a volume of the voxel i, and $\sum_{j=1}^{N} v_j$ is the total volume of all voxels in the OAR structure. The residual driver can be a constant or function based on target objective function value(s). The OAR goal 116 received or input includes the EUD level ($EUD_g$), the priority/weight ($w^k$), and the level of sparing (c). In one embodiment the level of sparing is a constant or a function of the EUD level. The level of sparing can be a value of the EUD level where $c < EUD_g$ or expressed as a function of the EUD level, such as a percentage.

A gradient function of the maximum EUD OAR modified objective function, a derivative of the maximum EUD OAR modified objective function with an offset to the EUD goal volume, has the effect of increasing a push or decreasing the planned dose to reach the EUD goal. Once the EUD goal is met the residual driver decreases the planned dose below the EUD goal and can be defined by:

$$\frac{\partial F(EUD^k, EUD_{go})}{\partial d_i} = \qquad \text{EQUATION 7}$$
$$\frac{2 w^k w_i v_i (EUD^{k-a} - d_i^{a-1})(EUD^k - EUD_{go})}{EUD_{go}^2}.$$

The target objective functions use either a standard uniform dose objective function or a pair of minimum dose and maximum dose objective functions. For example, a maximum/minimum dose objective function can be defined by:

$$F^k = w^k \sum_{i \in V} f(d_i, d_g) \left( \frac{d_i - d_g}{d_g} \right)^2 \Delta v_i,$$

EQUATION 8 where $f(d_i,d_g)=H(d_i-d_g)$ for the maximum dose objective function, $f(d_i,d_g)=d_g-d_i)$ for the minimum dose objective function, and H is the Heaviside function. The target goals received or input, include a first dose goal level ($d_g$), a priority/weight for the target structure, and a second dose goal level ($d_{hs}$) where $d_g \leq d_{hs}$. The first dose goal level operates as a minimum dose goal for the corresponding target structure and the second dose level operates as a maximum dose goal for the corresponding target structure. In one embodiment, the first dose goal level include a minimum dose to a given volume (Min DVH), and a second dose goal level includes a maximum dose to a given volume (Max DVH). In some instances, the Min DVH/Max DVH allow a certain percentage of the target structure to have hot spots.

In one embodiment, the target objective function includes a modified objective function similar to EQUATION 1 and EQUATION 2, changing the objective based on an increasing dose or dose minimum, and a push of the residual driver operates where the first dose goal is met to increase the planned dose above the dose goal. In one embodiment, the objective weight for offending voxels is increased to drive those voxels within range, which enforces the second dose goal level ($d_{hs}$). In one embodiment, the second dose goal level is a constant or a function of the first dose goal. The increase can be a single increase or an incremental increase based on optimization iteration number, voxel dose, or other parameter.

The RT optimization unit 124 can include parameter tuning. The parameter tuning includes changing the weight and/or the dose goal. The weight and/or dose goal change can be performed for the segmented structure or for each voxel. The tuning can be performed before or after each optimization iteration or in some other pattern, such as every other iteration, every $n^{th}$ iteration, or the iteration period can be defined an arbitrary function. In one embodiment, the iteration selected for tuning is based on a convergence level, such as the difference between successive current doses $|d_i-d_{i+1}|$, difference between the current dose and the goal dose $|d_i-d_g|$, and the like.

In one embodiment, OAR modified objective function weights can be controlled using the following equation:

$$W_i = \frac{W_{i-1} * OFValue_{goal}}{OFValue_i},$$

EQUATION 9 where W is the weight, i is the iteration number, and OFValue is the objective function value. $OFValue_{goal}$ is computed by optimizing only the target goals, e.g. excluding the OAR goals and then computing a percentage of the modified target objective function values using a product defined by:

$OFValue_{goal}=OFValue_{targets}*TargetOARBalance$  EQUATION 10 where TargetOARBalance is a constant that can be determined per modified target objective, based on weight of a goal, or some other method.

In one embodiment, modified objective functions are tuned independently where the dose goal has not been reached. For example, the push, e.g. decrease planned dose for OAR goals, increase planned dose for target goals, by the residual driver can be turned off by changing the dose goal of the modified objective function. Voxels outside any OAR structures, e.g. in other parts of the body region, can also be optimized in a similar way to the residual driver operation defined in a modified objective functions, which avoids driving the dose unwittingly into undefined regions of the body. In another embodiment, the residual driver of a modified objective function is applied to each voxel outside the target region by a margin, e.g. a dose fall off region. Dose in the fall off region is optimized with a separate objective such as the modified EUD or a modified maximum dose objective with varying max dose goals based on distance from the target(s).

A therapy control device 128 receives the optimized plan 126 and generates a set of control instructions 130 for the radiation delivery device 104, such as a Linear Particle Accelerator (LINAC), a proton therapy device and the like, to deliver the beams of external radiation to the subject using IMRT or VMAT.

The segmenter 108, the RT optimization unit 124, and the therapy control device 128 are suitably embodied by one or more configured data processors, such as the data processor 122, a distribution of processors include peer-to-peer or cooperatively operating processors, client-server arrangement of processors, and the like. The configured processor executes at least one computer readable instruction stored in computer readable storage medium ("memory") 132, which excludes transitory medium and includes physical memory and/or other non-transitory medium to perform the disclosed segmentation, optimization, and control instruction generation techniques. The configured processor may also execute one or more computer readable instructions carried by a carrier wave, a signal or other transitory medium.

Figure 2:
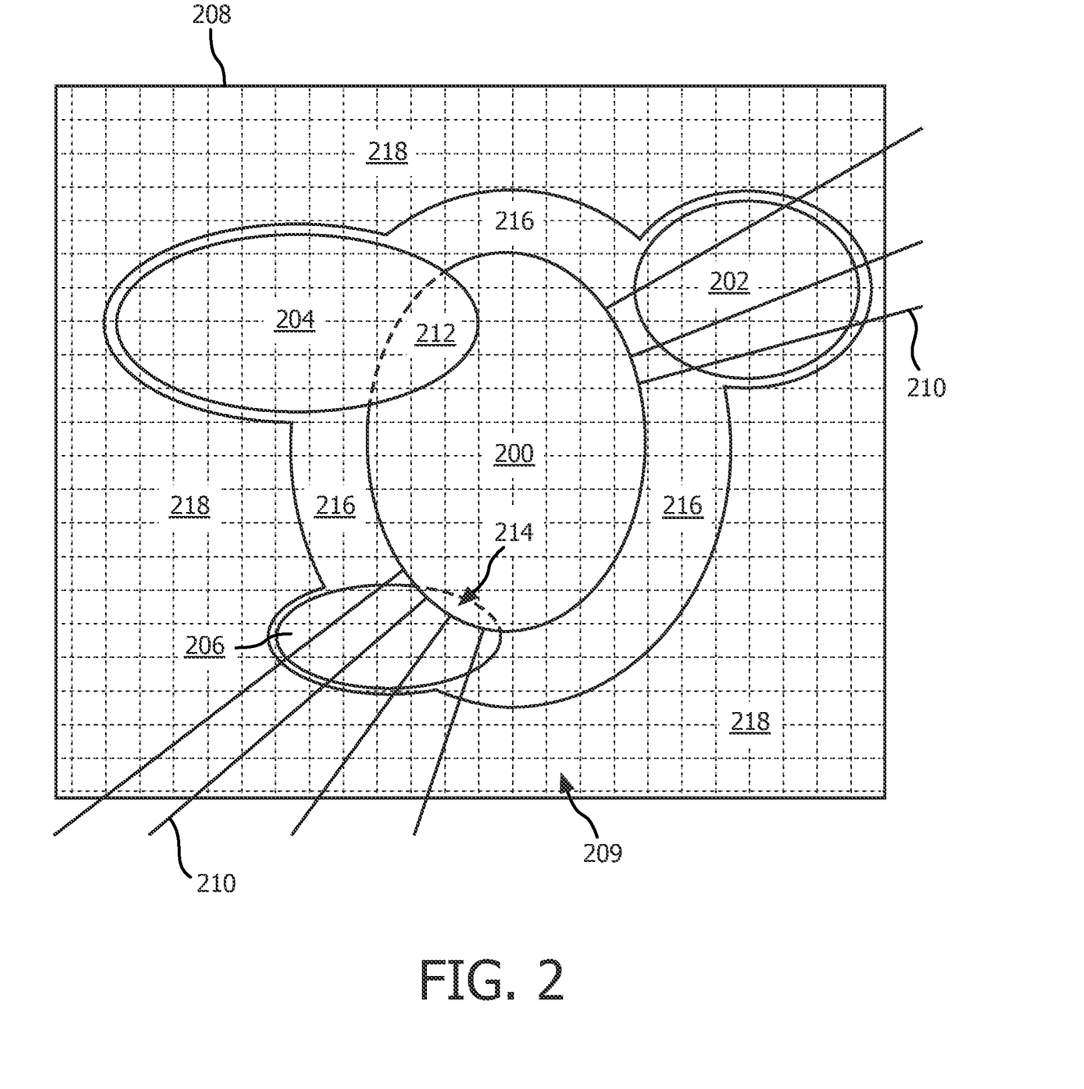
FIG. 2 shows an example conceptual two dimensional display of structures in a body volume.

With reference to FIG. 2 an example conceptual two dimensional display of a target structure 200 and OAR structures 202, 204, 206 in a volume 208 is shown with a dose grid 209. A first OAR structure 202 is separated from the target structure 200. Conceptually, the first OAR structure 202 is indicated as a parallel organ by beams of radiation 210, which pass through the volume, e.g. the parallel organ can receive a radiation dose which sacrifices a portion of the OAR volume to achieve the dose goal for the target structure 200. A global consideration is to reduce the radiation delivered to the first OAR structure 202 where possible below the dose goal for the first OAR structure 202.

A second OAR structure 204 overlaps the target structure 200 in an overlap region 212. The second OAR structure 204 is conceptually represented as a serial organ, and a global consideration is that radiation is to be minimized to the serial organ including the overlap region 212. Another global consideration is not to sacrifice any portion of the serial organ and to push the dose below the dose goal where possible. The global considerations are implemented by weighting the voxels in the second OAR structure 204 including the overlap region 212 for the maximum dose OAR modified objective function, e.g. set to one, while the weighting of the voxels in the overlap region 212 for the target objective function or target modified objective function are given no weight, e.g. set to zero.

A third OAR structure 206 overlaps the target structure 200 in a second overlap region 214. The third OAR structure 206 is conceptually represented as a parallel organ and although radiation is to be minimized where possible, the target structure 200 is to receive the dose goal for the target structure including the overlap portion 214. Another global consideration that at least the overlap portion 214 is considered part of the target structure 200 and portions of the third OAR structure 206 can be sacrificed. Another global consideration is that were possible, the dose can be reduced below the dose goal for the third OAR structure 206, which in some instances has the effect of not sacrificing the parallel organ or fewer portions of the parallel organ. The voxels in the overlap region 214 are weighted according to the target objective function or target modified objective function. In one embodiment, the voxels are weighted in a gradient form or dose drop off by distance, which transitions the weight from that of the target structure 200 with the edge of the overlap region 214 adjacent the target structure 200 to the edge of the third OAR structure 206 and the weight according to the maximum EUD OAR modified objective function for the third OAR structure 206.

Voxels in a dose fall off region 216, which is a geometric region between and around target structures, includes dose goals reduced from the target structure 200. The dose fall off region 216 includes voxels in a distance from the target structure 200. In one embodiment the dose fall off region 216 includes a dose fall off per distance or dose fall off rate, e.g. centiGray/centimeter (cGy/cm). For example, the dose goal is reduced by 50% from the dose goal of the target structure 200 or other healthcare practitioner specified amount. In another example, the dose goal for voxels varies by distance from the target structure 200 until a 50% reduction is achieved. A global consideration is target conformality and reducing overall body dose. For example, radiation is to be delivered to volumes represented by each voxel in the target structures and ensuring coverage of the target structures while minimizing the overall body dose. The dose fall off region can include OARs adjacent or within the dose fall off region 216. As shown in the example, the first OAR structure 202, the second OAR structure 204, and the third OAR structure 206 are included in the dose fall off region 216. The dose falloff region does not have to be geometrically uniform in thickness and the dose fall off per distance can vary throughout the region.

Voxels in the dose fall off region 216 are optimized to different maximum dose levels relative to their proximity to a target structure and the minimum target dose goals. Voxels closer to the target structure have a higher maximum dose level than voxels farther away. Also, voxels adjacent to a higher dose target have a higher maximum dose level than voxel adjacent to lower dose targets.

A body region 218 includes voxel volumes outside of the target structure 200, OAR structures 202, 204, 206, and the dose falloff region 216. A maximum body dose goal is received or input similar to the OAR goals and includes a dose goal level and a weight. The body region can automatically determined and included as a new structure. The maximum dose OAR modified objective function minimizes the dose to the body and globally considers avoidance of hot spots. In one embodiment, the structures of the dose fall off region 216 and the body region 218 are combined with different voxel weighting and the maximum EUD and or maximum dose OAR modified objective function minimizes the body dose. Voxels closest to the target structure include a lower weight than voxels further away.

Figure 3:
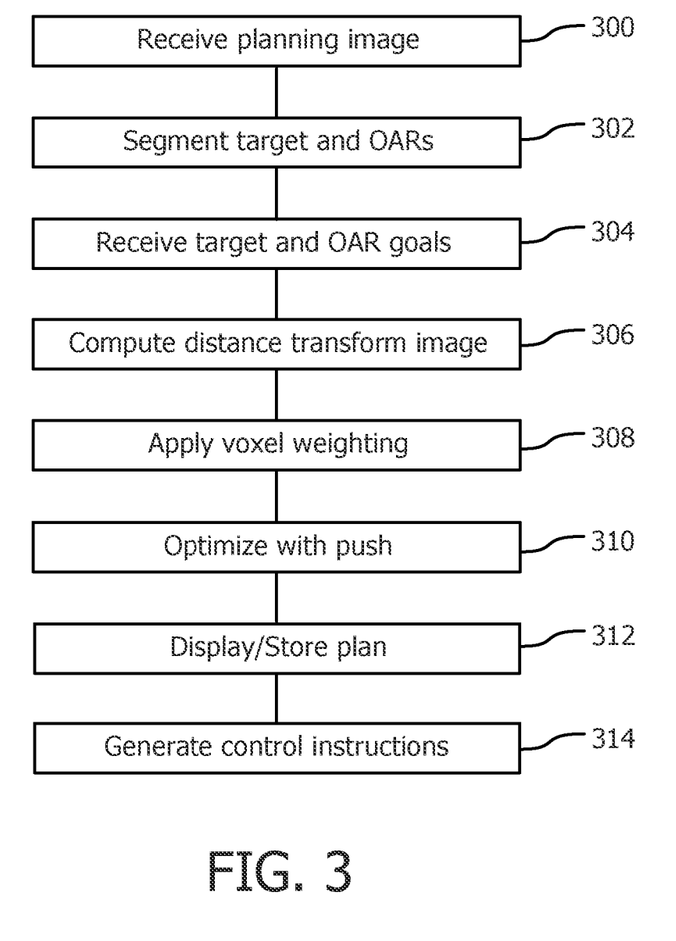
FIG. 3 illustrates an example method for radiation therapy planning with the RT optimization unit.

With reference to FIG. 3, an example method for radiation therapy planning with the RT optimization unit 124 is illustrated. At 300, the volumetric planning image 106 is received. The planning image 106 can be received from the imaging device 102 or from storage.

At 302, target structures and OAR structures are segmented by the segmenter 108. Target structure dose goals and weights, and OAR structure dose goals and weights are received at 304. A body dose goal and fall off dose goals can also be received at 304.

At 306, a distance transform image is computed by the RT optimization unit 124, which for each voxel provides a distance from at least a nearest target structure. The structure or structures for the body region and the dose fall off region are constructed based on the computed distances.

Voxel weighting is computed and assigned at 308 by the RT optimization unit 124 and objective functions are associated with the weighted voxels. Voxel weighting is computed initially according to the segmented structure(s) and can be modified by the computed distances. For example, weights for voxels representing OAR structures are assigned from the weight according to the segmented OAR structure. Weights for voxels representing parallel structures which include overlapping regions are applied from the target structures and can include a dose fall off for the overlapping region. Weights from the dose fall off region and the body region are applied according to received weights and the voxels in the dose fall off region are modified by the computed distances.

The RT optimization unit 124 generates an optimized plan, which includes a set of planned external radiation beams based on at least one modified objective function and associated planned doses for each voxel. For the maximum OAR modified objective functions and/or the maximum EUD OAR modified objective function, once the goal is met, the RT optimization unit 124, where possible, pushes or decreases the dose lower and/or adjusts the goal dose through tuning. For target modified objective functions, the RT optimization unit 124, where possible, pushes or increases the dose higher. The RT optimization unit 124 can adjust the weighting and/or the dose goal for the voxels between iterations.

At 312, the generated set of planned external radiation beams and/or a planned dose based on the set of planned external radiation beams can be displayed and/or stored in a storage device, e.g. computer memory. The planned dose can be display superimposed on the planning image 106, such as with iso-contours. The segmented structures, dose fall off region and/or body region can be indicated on the display, such as with a contrast or color maps.

The therapy control device 128 can generate control instructions for the radiation delivery device 104 at 314 based on the generated set of planned external radiation beams.

The above may be implemented by way of computer readable instructions, encoded or embedded on computer readable storage medium, which, when executed by a computer processor(s), cause the processor(s) to carry out the described acts. Additionally or alternatively, at least one of the computer readable instructions is carried by a signal, carrier wave or other transitory medium.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A radiation therapy planning system, comprising:
   a radiation therapy (RT) optimization unit comprising a processor, the RT optimization unit configured to:

receive at least one target structure and at least one organ-at-risk (OAR) segmented from a volumetric image;

weight voxels according to a distance from a nearest one of the at least one target structure;

receive a first dose goal for one of the at least one organ-at-risk; and generate an optimized plan based on at least one modified objective function comprising a maximum organ-at-risk modified objective function associated with voxels in the one of the at least one organ-at-risk, the optimized plan comprising a planned radiation dose for each voxel, wherein generating the optimized plan comprises decreasing the planned radiation dose for at least one voxel below the received first dose goal based on the maximum organ-at-risk modified objective function, when the first dose goal is met.

2. The radiation therapy planning system according to claim 1, wherein the RT optimization unit is further configured to receive, a first weight, and a first level of sparing for one of the at least one organ-at-risk.

3. The radiation therapy planning system according to claim 2, wherein the RT optimization unit is further configured to receive a second dose goal, a second weight, and a second level of sparing for one of the at least one organ-at-risk, and one of the at least one modified objective function comprises a maximum organ-at-risk equivalent uniform dose modified objective function associated with voxels in the one of the at least one organ-at-risk.

4. The radiation planning therapy system according to claim 1, wherein the RT optimization unit is configured to adjust at least one of a first weight, a second weight, the first dose goal, and a second dose goal between iterations of optimization for at least one voxel in the volumetric image.

5. The radiation therapy planning system according to claim 1, wherein the RT optimization unit is configured to generate a dose fall off region structure which comprises a geometric volume of voxels surrounding the at least one target structure a distance from the at least one target structure, and associates a modified objective function with the dose fall off region structure.

6. The radiation therapy planning system according to claim 5, wherein the RT optimization unit is configured to generate a body region structure which comprises a volume of voxels in the body region structure excluding voxels in the dose fall off region, the at least one target structure, and the at least one organ-at-risk, and to associate the maximum organ-at-risk modified objective function with the body region structure and a received third dose goal.

7. The radiation therapy planning system according to claim 1, wherein the at least one target structure and the at least one organ-at-risk comprise an overlapping region of voxels, and the planned radiation dose in the overlapping region of voxels is computed according to at least one of:
the maximum organ-at-risk modified objective function weighted according to received dose goals of the at least one organ-at-risk; or
a maximum organ-at-risk equivalent uniform dose modified objective function weighted according to a distance from an edge of the overlapping region of voxels and received dose goals of the at least one target structure.

8. The radiation therapy planning system according to claim 1, wherein the RT optimization unit is configured to fit a dose grid to a volume of the volumetric image and compute planned doses in iterations for a group of spatially adjacent voxels, which in subsequent iteration are processed as volumes of individual voxels; and further comprising:

a radiation delivery device configured to deliver a set of external radiation beams to the at least one target structure according to the optimized plan.

9. A method of radiation therapy planning, comprising:
segmenting at least one target structure and at least one organ-at-risk from a volumetric image;

weighting voxels according to a distance from a nearest one of the at least one target structure;

receiving a first dose goal for one of the at least one organ-at-risk; and generating an optimized plan based on at least one modified objective function, and the optimized plan comprises a planned radiation dose for at least one voxel, wherein one of the at least one modified objective function comprises a maximum organ-at-risk modified objective function associated with voxels in the one of the at least one organ-at-risk, and wherein generating based on the maximum organ-at-risk modified objective function decreases the planned radiation dose for the at least one voxel below the received dose goal, when the received first dose goal is met.

10. The method according to claim 9, further comprising:
receiving, a first weight, and a first level of sparing for the one of the at least one organ-at-risk.

11. The method according to claim 10, further comprising:
receiving a second dose goal, a second weight, and a second level of sparing for one of the at least one organ-at-risk, and one of the at least one modified objective function comprises a maximum organ-at-risk equivalent uniform dose modified objective function associated with voxels in the one of the at least one organ-at-risk.

12. The method according to claim 9, wherein generating comprises adjusting at least one of a first weight, a second weight, a first dose goal and a second dose goal between iterations of optimization for at least one voxel.

13. The method according to claim 9, wherein generating comprises generating a dose fall off region structure, which comprises a geometric volume of voxels surrounding the at least one target structure a distance from the at least one target structure, and associating a modified objective function with the dose fall off region structure.

14. The method according to claim 13, wherein generating comprises generating a body region structure, which comprises a volume of voxels in the body region structure excluding voxels in the dose fall off region, the at least one target structure, and the at least one organ-at-risk, and associating the maximum organ-at-risk modified objective function with the body region structure and a received third dose goal.

15. The method according to claim 9, further comprising controlling a radiation delivery device with the optimized plan to deliver a set of external radiation beams to the at least one target structure.

16. A therapy control device for radiation therapy (RT) optimization, comprising:
a processor;
a tangible and non-transitory memory that stores instructions, which when executed by the processor, cause the processor to:
receive at least one target structure and at least one organ-at-risk (OAR) segmented from a volumetric image;
weight voxels according to a distance from a nearest one of the at least one target structure;

receive a first dose goal for one of the at least one organ-at-risk; and generate an optimized plan based on at least one modified objective function comprising a maximum organ-at-risk modified objective plan associated with voxels in the one of the at least one organ-at-risk, the optimized plan comprising a planned radiation dose for each voxel, wherein generating the optimized plan comprises decreasing the planned radiation dose for at least one voxel below the received first dose goal based on the maximum organ-at-risk modified objective function, when the first dose goal is met.

17. The therapy control device according to claim 16, wherein the tangible and non-transitory memory stores further instructions, which when executed by the processor, cause the processor to receive, a first weight, and a first level of sparing for one of the at least one organ-at-risk.

18. The therapy control device according to claim 16, wherein the at least one target structure and the at least one organ-at-risk each comprise an overlapping region of voxels, and the planned radiation dose in the overlapping region of voxels is determined based on at least one of:

the maximum organ-at-risk modified objective function weighted according to received dose goals of the at least one organ-at-risk; or a maximum organ-at-risk equivalent uniform dose modified objective function weighted according to a distance from an edge of the overlapping region of voxels and received dose goals of the at least one target structure.

19. The therapy control device according to claim 16, wherein the tangible and non-transitory memory that stores further instructions, which when executed by the processor, cause the processor to:

fit a dose grid to a volume of the volumetric image and compute planned doses in iterations for groups of spatially adjacent voxels, which in subsequent iterations are processed as volumes of individual voxels; and generate a set of control instructions that cause a radiation delivery device configured to deliver a set of external radiation beams to the at least one target structure according to the optimized plan.

* * * * *